United States Patent
Walker et al.

(10) Patent No.: US 8,166,804 B2
(45) Date of Patent: May 1, 2012

(54) METHOD FOR DETECTING SEPARATION IN A STRUCTURE

(75) Inventors: Lawrence John Walker, Karrinyup (AU); Nigel Laxton, Mt. Hawthron (AU)

(73) Assignee: Structural Monitoring Systems Ltd., Osborne Park, WA (AU)

( * ) Notice: Subject to any disclaimer, the term of this patent is extended or adjusted under 35 U.S.C. 154(b) by 603 days.

(21) Appl. No.: 12/296,076

(22) PCT Filed: Apr. 4, 2007

(86) PCT No.: PCT/AU2007/000456
§ 371 (c)(1),
(2), (4) Date: Oct. 3, 2008

(87) PCT Pub. No.: WO2007/112512
PCT Pub. Date: Oct. 11, 2007

(65) Prior Publication Data
US 2009/0113994 A1    May 7, 2009

(30) Foreign Application Priority Data

Apr. 4, 2006  (AU) .............................. 2006901756

(51) Int. Cl.
*G01N 19/08*     (2006.01)
*G01M 3/26*     (2006.01)
(52) U.S. Cl. ................... 73/86; 73/38; 73/46; 73/865.8; 73/866.5
(58) Field of Classification Search ................ 73/37, 38, 73/40, 46, 865.8, 866.5
See application file for complete search history.

(56) References Cited

U.S. PATENT DOCUMENTS

| | | | | |
|---|---|---|---|---|
| 2,185,315 A | * | 1/1940 | Rogatchoff | 116/200 |
| 2,694,924 A | * | 11/1954 | Matloclk et al. | 73/37 |
| 3,820,381 A | * | 6/1974 | Thurston | 73/40 |
| 4,104,906 A | | 8/1978 | Oertle | |
| 4,135,386 A | | 1/1979 | Peterson et al. | |
| 4,145,915 A | | 3/1979 | Oertle et al. | |
| 4,254,415 A | * | 3/1981 | Kaufman | 340/679 |
| 4,345,457 A | * | 8/1982 | Kuroki et al. | 73/37.5 |
| 4,448,080 A | * | 5/1984 | Dressel et al. | 73/799 |
| 4,513,605 A | * | 4/1985 | Hawerkamp | 73/40 |

(Continued)

FOREIGN PATENT DOCUMENTS
WO    01/98746 A1    12/2001

OTHER PUBLICATIONS

International Search Report for parent application PCT/AU2007/000456, having a mailing date of May 17, 2007.

*Primary Examiner* — David Rogers
(74) *Attorney, Agent, or Firm* — Andrus, Sceales, Starke & Sawall, LLP

(57) ABSTRACT

A method for detecting separation in a structure that comprises at least two portions or layers affixed together comprises forming a cavity into the structure that passes through an interface formed between the two portions and plumbing the cavity to a monitoring system. A pressure differential is established between the cavity and a reference pressure to which the structure is exposed. A monitoring system monitors for a change in the pressure state of the cavity. Changes in the pressure state are indicative of a separation between the portions or layers.

11 Claims, 4 Drawing Sheets

U.S. PATENT DOCUMENTS

| | | | |
|---|---|---|---|
| 4,806,913 A * | 2/1989 | Schmidt | 340/679 |
| 4,979,390 A * | 12/1990 | Schupack et al. | 73/38 |
| 5,263,362 A * | 11/1993 | Karl et al. | 73/46 |
| 5,559,282 A * | 9/1996 | Knight et al. | 73/40 |
| 5,770,794 A | 6/1998 | Davey | |
| 6,539,776 B2 * | 4/2003 | Davey | 73/37 |
| 6,591,661 B2 * | 7/2003 | Davey | 73/38 |
| 6,615,642 B2 * | 9/2003 | Poblete | 73/37 |
| 6,715,365 B2 | 4/2004 | Davey | |
| 6,823,719 B2 * | 11/2004 | Poblete | 73/46 |
| 7,500,383 B2 * | 3/2009 | Davey | 73/49.2 |
| 7,559,250 B2 * | 7/2009 | Seitz et al. | 73/799 |
| 2002/0029614 A1 | 3/2002 | Davey | |
| 2002/0038568 A1 * | 4/2002 | Davey | 73/38 |
| 2007/0107496 A1 * | 5/2007 | Davey | 73/38 |
| 2008/0183403 A1 * | 7/2008 | Cipra | 702/34 |
| 2010/0001874 A1 * | 1/2010 | Cipra | 340/683 |
| 2010/0005862 A1 * | 1/2010 | Davey et al. | 73/46 |
| 2010/0107768 A1 * | 5/2010 | Elze et al. | 73/627 |

* cited by examiner

US 8,166,804 B2

METHOD FOR DETECTING SEPARATION IN A STRUCTURE

FIELD OF THE INVENTION

The present invention relates to a method for detecting separation in a structure.

BACKGROUND OF THE INVENTION

It is known that structures having two or more portions that are affixed together can separate during the service life of the structure. For example, in a laminate structure, separation by delamination of the strata within the laminate can occur. There are many causes of separation, including the bond joining portions of the structure weakening over time, impurities in the material, and excessive stress experienced when the structure is under load.

Known methods for non-destructive testing (NDT) of a structure for separation include frequency-response analysis, in which the resonant modal frequencies of the structure in response to an excitation vibration are analyzed.

Another NDT method involves laser shearography, in which a surface is measured using a laser with and without an applied load in order to measure the geometry difference.

Another alternative NDT method for testing for delamination involves delamination thermography, in which heat transfer through a structure is used to determine discontinuities or air gaps within the structure.

These methods are relatively effective for detecting separation. However, it is recognized that difficulties arise when attempting to employ these methods while the structure is in situ, or in operation.

SUMMARY OF THE INVENTION

According to a first aspect of the present invention there is provided a method for detecting separation in a structure that has at least two elements that are affixed in a sealing manner together, the method comprising:
  forming a cavity within the structure that extends from an opening on a first surface of the structure and passes through an interface between adjacent elements within the structure;
  plumbing the blind hole into a monitoring system;
  establishing a pressure differential between the cavity and a reference pressure adjacent the cavity; and
  monitoring for a change in the pressure state of the cavity.

According to a second aspect of the present invention there is provided a method for detecting delamination in a structure that has at least two strata that are laminated together, the method comprising:
  forming a cavity within the structure that extends from an opening on a first surface of the structure and passes through an interface of adjacent strata within the structure;
  plumbing the cavity into a monitoring system;
  establishing a pressure differential between the cavity and a reference pressure adjacent the cavity; and
  monitoring for a change in the pressure state of the cavity, which is indicative of delamination of the structure.

A method for detecting failure in a bond at an interface between adjacent layers of polymer composite materials in a structure composed of a plurality of mutually overlying and bonded layers of polymer composite material, the method comprising:
  forming a cavity in the composite structure that opens onto one surface of the composite structure and extends across one or more interfaces of the composite structure wherein at least one of the interfaces opens onto the cavity;
  sealing an end of the cavity distant the first surface;
  plumbing an end of the cavity adjacent the first surface to a monitoring system;
  establishing a pressure differential between the cavity and a reference pressure to which the interface is exposed; and
  monitoring for a change in pressure in the cavity.

BRIEF DESCRIPTION OF THE DRAWINGS

In order that the invention may be more easily understood, embodiments will now be described, by way of example only, with reference to the accompanying drawings, in which.

DETAILED DESCRIPTION OF THE PREFERRED EMBODIMENTS

Figure 1:
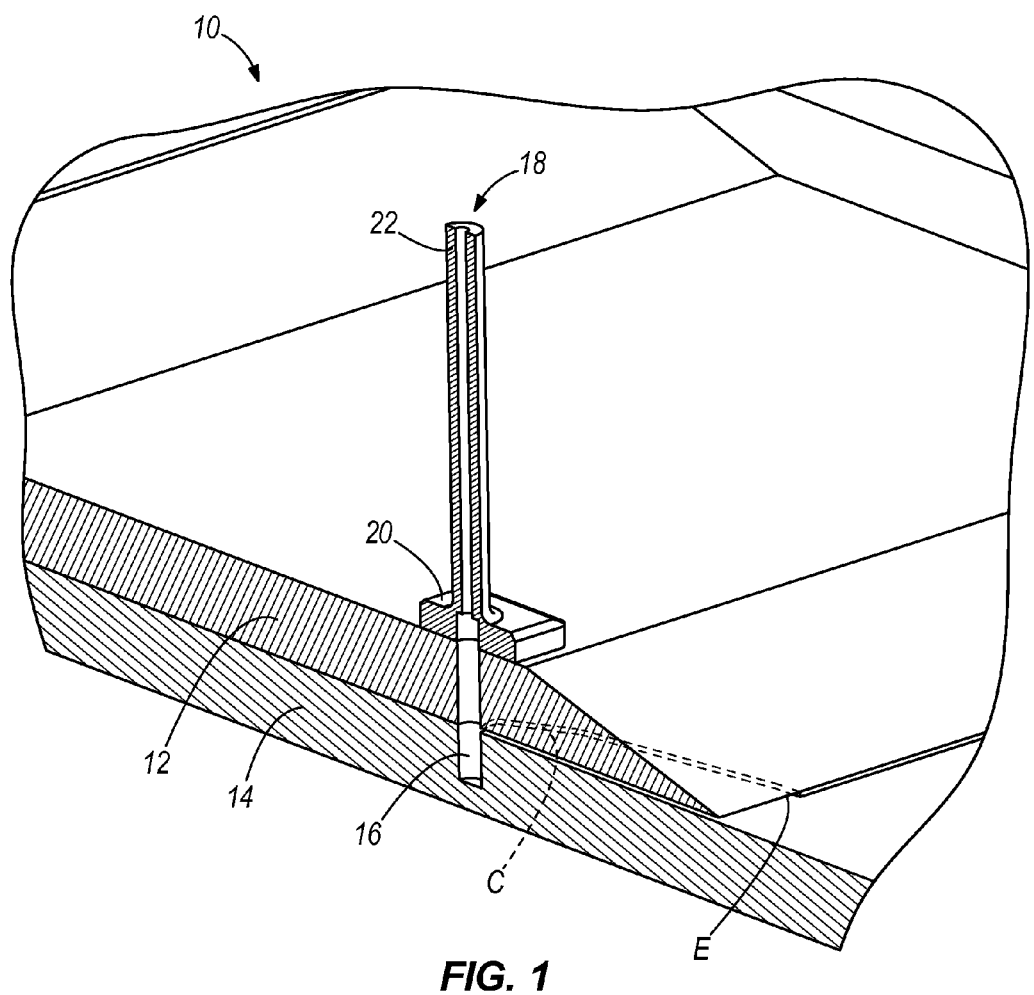
FIG. 1: is a cross sectional axonometric view of a laminate structure and connector in relation to which a first embodiment of the method according to the present invention.

FIG. 1 shows a structure 10 that has a first element, in the form of a first stratum 12, and a second element, which is in the form of a second stratum 14. The first and second strata 12, 14 are affixed to one another in a sealing manner. In this embodiment, the first stratum 12 is laminated to the second stratum 14. The structure 10 has a cavity, which in this embodiment is defined by a blind hole 16 that extends through the first stratum 12 and partially through the second stratum 14. Accordingly, the blind hole 16 passes through the interface between the first and second strata 12, 14.

A connector 18 is attached and sealed to the first stratum 12. In this embodiment, the connector 18 is in the form of a flanged portion 20 and a tube 22 that extends from the flanged portion 20. The tube 22 defines a throughway or passage that extends through the connector 18. The flanged portion 20 is attached and sealed to the first stratum 12 about the opening of the blind hole 16 such that the throughway registers with the blind hole 16 and a substantially hermetic seal is formed between the flanged portion 20 and the first stratum 12.

The connector 18 enables the blind hole 16 to be plumbed into a differential pressure monitoring system (not shown). The monitoring system may be a relative negative (or vacuum) pressure system as described in U.S. Pat. No. 5,770,794 or a relative positive pressure system as described in US 2002/0029614, the contents of both of which are incorporated herein by way of reference. Tubing, such as flexible piping, may be used to plumb the cavity formed by the blind hole 16 to other elements of the differential pressure monitoring system, such as a monitoring instrument and other sensor elements can be attached to the tube 22.

In practice, the differential pressure monitoring system is operated such that the pressure within the blind hole 16 is non-atmospheric relative to the atmosphere surrounding the structure 10. Accordingly, the blind hole 16 may be either at least partially evacuated to establish a relative vacuum or pressurized to establish a relative positive pressure.

As shown in FIG. 1, the first and second strata 12, 14 have partially separated due to a crack C forming through a portion of the interface between the first and second strata 12, 14. The crack C can arise by delamination of a portion of the structure 10. In this example, the crack C extends from the blind hole 16, along the interface between the first and second strata 12, 14 and opens onto an external end region E of the laminated portion of the structure 10.

As stated previously, in this embodiment the pressure within the blind hole 16, prior to the formation of the crack C, is non-atmospheric, such that a pressure differential exists between the blind hole 16 and a reference pressure to which the end region E of the structure 10 is subject, which in this embodiment is ambient atmospheric pressure surrounding the structure 10. The pressure differential is maintained (prior to formation of the crack) because the elements/strata 12, 14 are sealed together. The sealing can be achieved by placing a sealant there between, the sealant may also constitute an adhesive that attaches or couples the elements together. The presence of the crack C can allow fluid to flow between the blind hole 16 and the surrounding atmosphere. The fluid flow will cause a change in the pressure state within the blind hole 16. The fluid flow and/or change in pressure state can be measured by the monitoring instrument. Furthermore, the fluid flow and/or change in pressure state can be indicative of the presence of a crack C within the structure 10.

Figure 2:
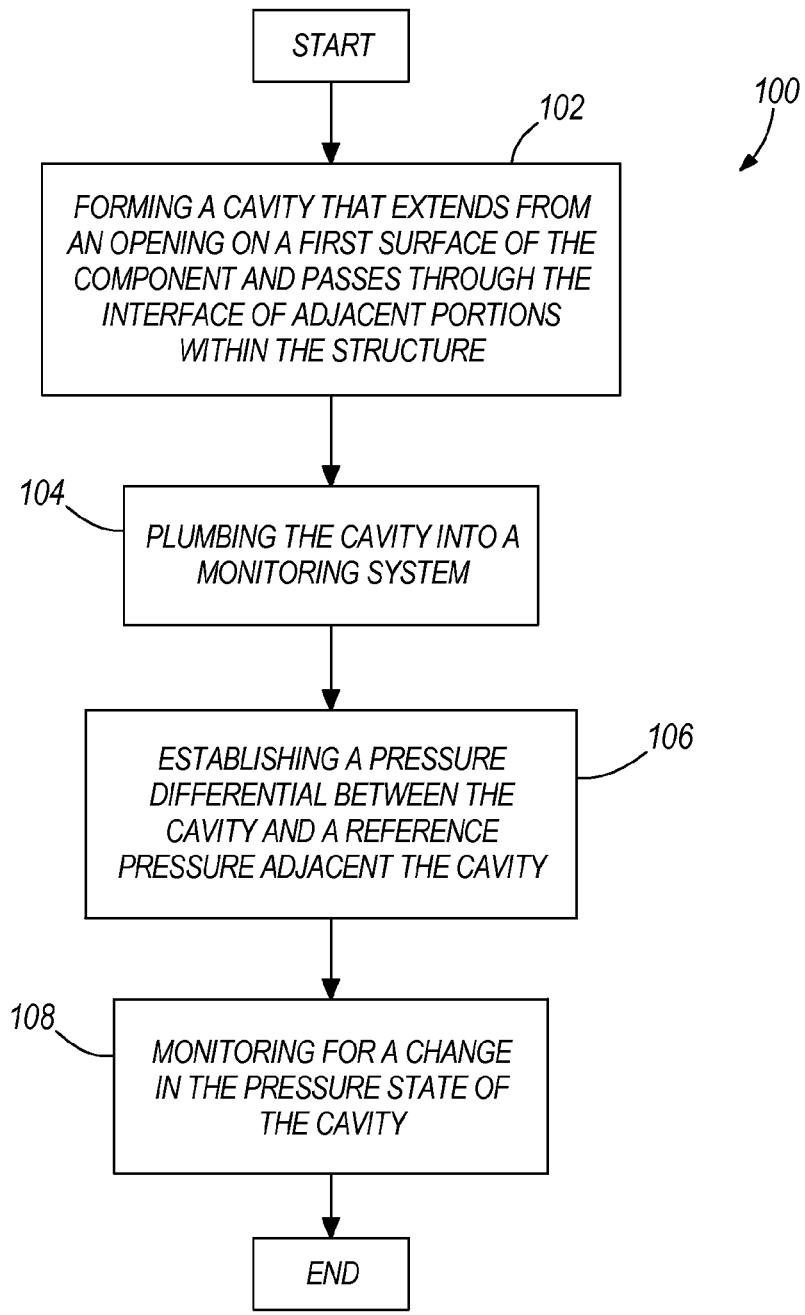
FIG. 2: is a flow chart of a method in accordance with a second embodiment of the present invention.

FIG. 2 shows a method 100 for detecting separation in a structure in accordance with a second embodiment, the structure having at least two elements that are affixed in a sealing manner together. The method includes the step 102 of forming a cavity within the structure that extends from an opening on a first surface of the structure and passes through an interface of adjacent elements within the structure.

Step 104 involves plumbing the blind hole into a monitoring system. Step 106 involves establishing a pressure differential between the cavity and a reference pressure adjacent the cavity. The reference pressure may pressure above or below atmospheric pressure, or may be atmospheric pressure.

The method 100 further involves the step 108 of monitoring for a change in the pressure state of the cavity. The change in the pressure state of the cavity is indicative of separation of elements within the structure.

Figure 3:
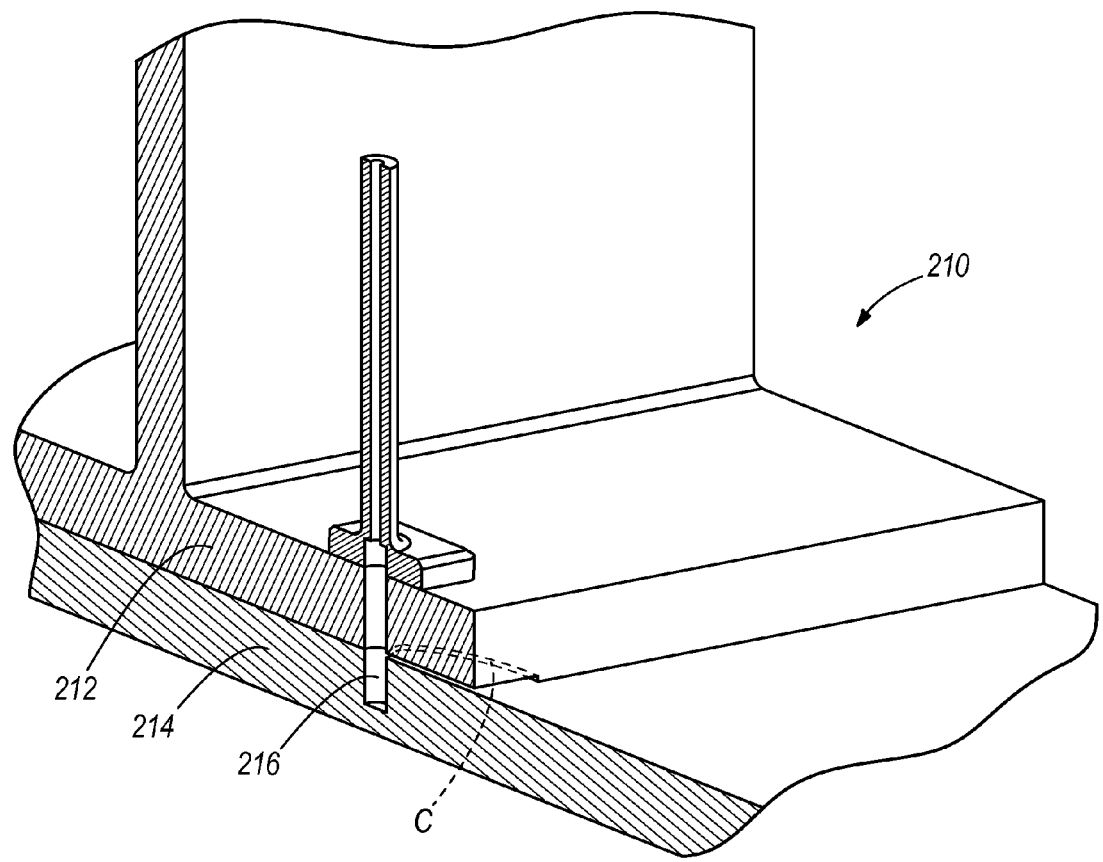
FIG. 3: is a cross sectional axonometric view of a bonded structure and connector in relation to which a third embodiment of the present invention may be applied.

FIG. 3 shows a structure 210 that has a first portion 212, in the form of a stringer of an aircraft, and the second portion 214 in the form of a skin of the aircraft. The first and second portions 212, 214 are affixed at the interface by, for example, a bond.

The structure 210 has a cavity, which in this embodiment is defined by a blind hole 216 that extends through the first portion 212 and partially through the second portion 214. Accordingly, the blind hole 216 is generally transverse to the interface of the first and second portions 212, 214, such that the blind hole 216 passes through the interface between the first and portions 212, 214.

A connector 18 is attached and sealed to the first stratum 212. In this embodiment, the connector 18 is substantially similar to the connector 18 of FIG. 1.

The connector 18 enables the blind hole 216 to be plumbed into a differential pressure monitoring system (not shown). Accordingly, tubing, such as flexible piping, that is used to plumb the cavity formed by the blind hole 216 to other elements of the differential pressure monitoring system, such as a monitoring instrument and other sensor elements can be attached to the tube 22.

In practice, the differential pressure monitoring system is operated such that the pressure within the blind hole 216 is non-atmospheric relative to the atmosphere surrounding the structure 210. Accordingly, the blind hole 216 may be either at least partially evacuated to establish a relative vacuum or pressurized to establish a relative positive pressure.

In the example shown in FIG. 3, a separation in the form of a crack C (which arises from a partial disbond of the first and second portions 212, 214) extends from the blind hole 216 through a portion of the interface between the first and second portions 212, 214 and opens to the environment surrounding the structure 210. The crack C defines a separation between the first and second portions 212, 214.

As stated previously, in this embodiment the pressure within the blind hole 216, prior to the formation of the crack C, is non-atmospheric, such that a pressure differential exists between the cavity defined by the blind hole 216 and a reference pressure adjacent the structure 210, which in this embodiment is the atmosphere surrounding the structure 210. The presence of the crack C can allow fluid to flow between the blind hole 216 and the surrounding atmosphere. The fluid flow will cause a change in the pressure state within the blind hole 216. The fluid flow and/or change in pressure state can be measured by the monitoring instrument. Furthermore, the fluid flow and/or change in pressure state can be indicative of the presence of a crack C within the structure 210.

It will be understood to persons skilled in the art of the invention that many modifications may be made without departing from the scope of the invention. For example, it is to be appreciated that in practice a crack C will not necessarily open onto an external end region of the affixed portions of the structure. Accordingly, in an alternative embodiment the structure may be provided with one or more second holes that are spaced apart from the blind hole and are maintained at a pressure level that is not equal to that of the blind hole. The second hole(s) can be simply open to the atmosphere. Alternatively, the second hole(s) can be maintained at a pressure that is non-atmospheric and not equal to the pressure in the blind hole. A crack that extends between the blind hole and any second hole (the blind hole and the second hole having a relative differential pressure) and through the interface between the first and second elements of the structure will cause a change in the pressure state of the blind hole, which is indicative of the presence of a crack.

It is to be appreciated that the connector may be of any desired shape and structure, provided that the connector fulfils the function of connecting the blind hole to the tubing that plumbs the blind hole into the monitoring system. Furthermore, the connector should also form a substantial hermetic seal.

In an alternative embodiment, the tubing to plumb the blind hole into the monitoring system may be affixed directly to first portion about the opening of the blind hole.

The first and second elements can be affixed to one another by any convenient method. For example, adhesives and/or sealants may be employed. Alternatively, in embodiments in which the first stratum and connector are made of plastics materials, plastic welding (either direct or indirect) may be employed. Alternatively, a bond using a combination of heat and pressure may be employed. In a further alternative, a solvent product may be delivered to one or both of the surfaces of the first stratum and flanged portion to be affixed. Upon contact the solvent product can fuse the structure and the connector together. In a further alternative, diffusion bonding may be employed. In any event the affixing of the elements is in a manner which creates a seal between adjacent elements.

Similarly, the connector can be affixed to the first portion by any convenient method.

In one alternative embodiment, the cavity may be created by forming a hole that extends entirely through the structure. Subsequently, a patch or similar sheet can be affixed to a surface of the structure to cover and seal the respective end of the hole. Thus, an effective blind hole is created in the structure.

It is to be appreciated that the cavity in the structure may have alternative configurations. For example, the cavity may be formed by a "V" or "U" shape, which have two openings on the surface of the structure. One of the openings may be closed off, such that an effective blind hole is created in the structure. Alternatively, both openings may be plumbed into the monitoring system.

It is to be appreciated that the structure may be any laminate structure that has two or more elements in the form of strata of any materials that are laminated together. For example, the method can readily be applied to a composite structure in which the strata are plies of fibers that are bonded by a cured plastics material. Delamination in such a composite structure may result in a crack that extends through the structure and between the plies.

Furthermore, it is to be appreciated that the structure may be made up of two or more components and/or sub-components.

Figure 4:
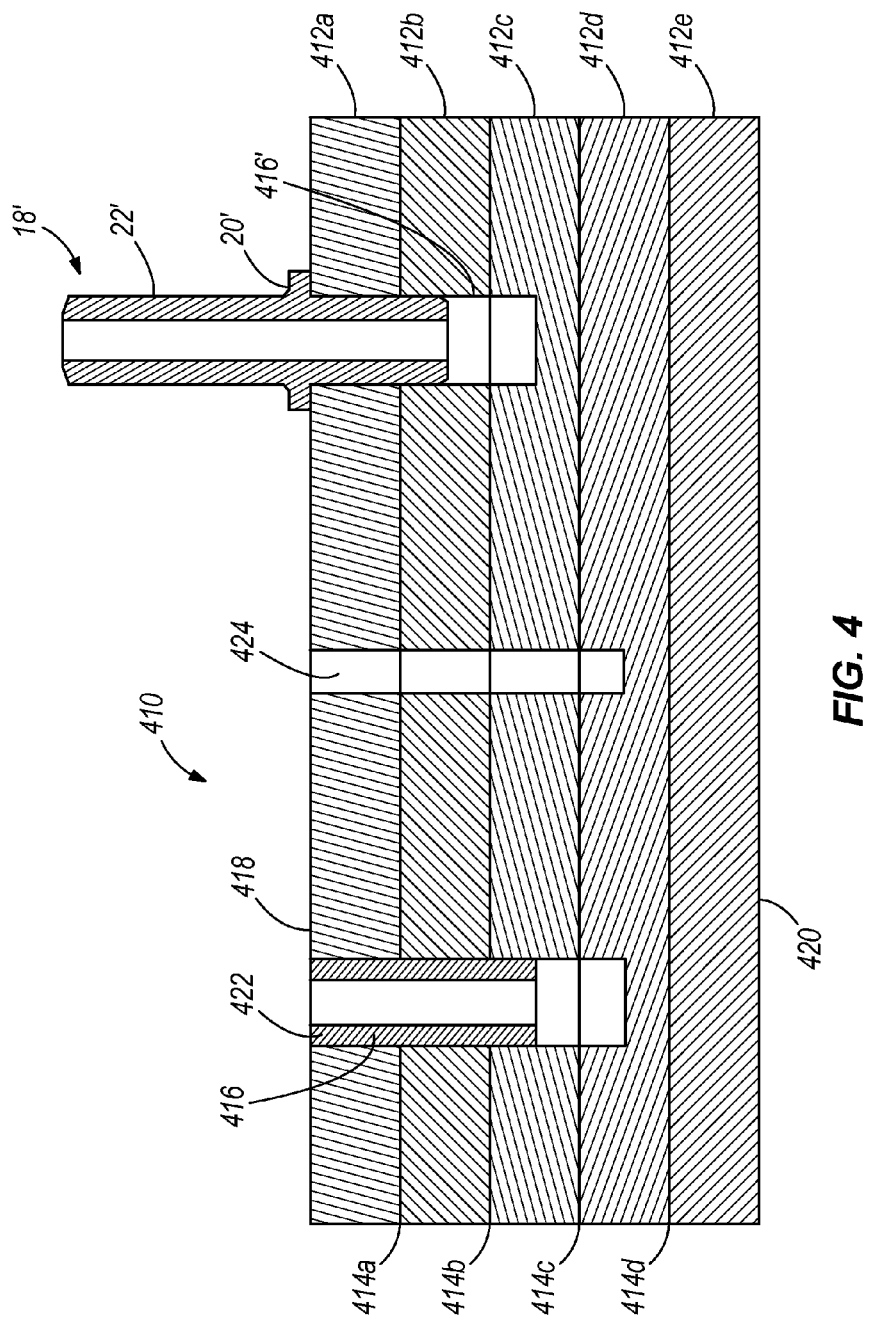
FIG. 4: is a cross sectional axonometric view of a structure and connector in relation to which a further embodiment of the invention may be applied.

In embodiments of the invention used in relation to multi-interface structures the blind hole(s) may be formed to target a particular interface to which the blind hole is open but sealed in relation to other non-target interfaces through which the hole passes. Consider for example a composite structure comprising say five plies of fiber reinforced polymer material, thus having four interfaces. A blind hole can be formed to target a specific interface. Thus one (or more) blind holes can be formed to target the first interface from a reference surface of the structure, another one or more blind holes can be formed to target the second interface from the reference structure, and so on. Any blind hole passing through a non-target interface can be sealed to the non-target interface. This can be achieved by placing a suitably dimensioned impervious sleeve into the blind hole which seals each of the non-target interfaces traversed by the blind hole, leaving only the target interface open to the blind hole. This is represented in FIG. 4 which shows a composite structure 410 having five layers 412a-412e (hereinafter referred to in general as "layers 412") of fiber bonded by curing the polymer. The layers 412 form four interfaces 414a-414d (hereinafter referred to as "interfaces 414"). The structure 410 has a first surface 418 parallel to the interfaces 414 and an opposite surface 420. In order to monitor for separation at target interface 414c formed by layers 412c and 412d a blind hole 416 is formed in the structure 410 from the first or reference surface 418 and terminates in the layer 412d. It would be appreciated that the hole 414 traverses the interfaces 414a and 414b as well as the target interface 414c. In order to ensure monitoring of only the interface 414c, a sleeve 422 is placed in the hole 416 and sealed to the circumferential surface of the hole 416. The sleeve 422 is dimensioned so as to terminate before the interface 414c so that the target interface 414c opens onto the hole 416. The sleeve 422 can be formed integrally with a connector 18 of the type hereinbefore described and illustrated in FIGS. 1 and 3. Alternately, the sleeve 422 can be formed separate from and subsequently coupled to a connector 18. Further holes can be formed in the structure 410 to target different interfaces 414. This enables one to monitor and detect separation in a specific layer or interface of a multi-interface structure.

An example of an integrated sleeve 422 and connector 18 is depicted as connector 18' in FIG. 4. Here the connector 18' includes a tail portion or sleeve 422' formed integrally with a tube portion 22' of the connector 18'. The sleeve portion 422' is of a length, or trimmed to be of a length, such that it penetrates into the blind hole 416' to a depth where it can seal the interface 414a but leaving the interface 414b unsealed and open onto the hole 416'. This enables the monitoring of the interface 414b.

In the embodiment described in relation to FIG. 4, one or more second blind holes 424 can be formed at spaced locations to the holes 416, 416', and pressurised to the reference pressure (or at least a different pressure to holes 416, 416') to enable detection of a crack or separation along an interface between the hole 416, 416' and the second hole 424. Further, the second hole 424 may be sealed to all but the target interface as per the holes/cavities 416, '416.

In a further embodiment where mechanical fasteners are used to either fix the elements of the structure 10 together, or to attach another component to the structure 10, the mechanical fastener can be formed with a passageway to enable the fastener to act as a connector 18, or as a "second hole" 424. In the latter case this may avoid the need to form "second holes" 424 solely for the purpose of admitting atmospheric pressure to the interfaces of the structure 10.

In the claims of this application and in the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

The invention claimed is:

1. A method for detecting failure in a bond at an interface between adjacent layers of polymer composite materials in a structure composed of three or more mutually overlying and bonded layers of polymer composite material, the method comprising:
    forming a cavity in the composite structure that opens onto a first surface of the composite structure and extends from the first surface into a layer of material below a target one of the interfaces and traversing one or more non-target interfaces wherein the target interface opens onto the cavity;
    sealing the non-target interfaces that open on to the cavity and an end of the cavity distant the first surface;
    plumbing an end of the cavity adjacent the first surface to a monitoring system;
    establishing a pressure differential between the cavity and a reference pressure to which the or each interface is exposed; and
    monitoring for a change in pressure in the cavity.

2. A method as claimed in claim 1, wherein the steps of establishing a pressure differential and monitoring for a change in the pressure state of the cavity are performed by a monitoring instrument.

3. A method according to claim 1 wherein sealing of the non-target interfaces comprises placing an impervious sleeve in the cavity and sealing an outer peripheral surface of the sleeve to the non-target interfaces.

4. A method as claimed in claim 1, wherein establishing a differential pressure involves forming a second cavity that extends from a second opening on a surface of the structure and passes through the or each interface of adjacent layers within the structure, the second cavity being spaced from the cavity.

5. A method as claimed in claim 4, wherein the wherein the structure comprises a plurality of second cavities.

6. A method as claimed in claim 1, wherein forming the cavity involves forming the cavity as a blind hole in the structure.

7. A method as claimed in claim 6, wherein establishing a differential pressure involves either (a) partially evacuating the cavity to a relative vacuum pressure, or (b) pressurising the cavity to a pressure greater than said reference pressure.

8. A method as claimed in claim 7, wherein the reference pressure adjacent the cavity is atmospheric pressure.

9. A method as claimed in claim 1, wherein plumbing the cavity into a monitoring system involves affixing a connector to the first surface about the opening and connecting tubing of the monitoring system to the cavity via the connector.

10. A method as claimed in claim 9, wherein the connector comprises a flanged portion that is affixed to the surface of the structure.

11. A method as claimed in claim 10, wherein the connector comprises a tube for connecting with the tubing of the monitoring system.

* * * * *